(12) United States Patent
Nowak

(10) Patent No.: US 11,375,989 B2
(45) Date of Patent: Jul. 5, 2022

(54) RETRACTOR SYSTEM, SWIVEL LOCK, AND SURGICAL RETRACTOR BLADE

(71) Applicant: Thompson Surgical Instruments, Inc., Traverse City, MI (US)

(72) Inventor: Steve Nowak, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 265 days.

(21) Appl. No.: 16/708,718

(22) Filed: Dec. 10, 2019

(65) Prior Publication Data

US 2021/0169462 A1 Jun. 10, 2021

(51) Int. Cl.
*A61B 17/02* (2006.01)
*A61B 17/00* (2006.01)

(52) U.S. Cl.
CPC ........... *A61B 17/0206* (2013.01); *A61B 2017/00367* (2013.01)

(58) Field of Classification Search
CPC ........... A61B 17/02; A61B 17/0206; A61B 2017/00367; A61B 2017/00371; A61B 2017/00389; A61B 2017/00393; A61B 2017/00477
USPC ................................................. 600/213, 234
See application file for complete search history.

(56) References Cited

U.S. PATENT DOCUMENTS

| | | |
|---|---|---|
| 3,749,088 A | 7/1973 | Kohlmann |
| 4,971,038 A | 11/1990 | Farley |
| 5,882,298 A | 3/1999 | Sharratt |
| 5,902,233 A | 5/1999 | Farley et al. |
| 5,931,777 A | 8/1999 | Sava |
| 5,944,736 A | 8/1999 | Taylor et al. |
| 5,976,171 A | 11/1999 | Taylor |

(Continued)

FOREIGN PATENT DOCUMENTS

| | | |
|---|---|---|
| EP | 1269922 | 1/2003 |
| ES | 2272170 | 4/2007 |

(Continued)

OTHER PUBLICATIONS

International Search Report and Written Opinion for PCT/US2020/060704, dated Feb. 2, 2021, 6 pages.

*Primary Examiner* — Eduardo C Robert
*Assistant Examiner* — Christina Negrellirodriguez
(74) *Attorney, Agent, or Firm* — McAndrews, Held & Malloy, Ltd.

(57) ABSTRACT

A retractor system includes a retractor arm and a retractor blade attached to the retractor arm via a swivel gear of a retractor blade connector. The retractor blade includes an attachment post extending through a port of the swivel gear. The retractor blade connector further includes a swivel gear detent and a plunger. The swivel gear detent is positioned to selectively engage the swivel gear and prevent the swivel gear and attached retractor blade from rotating about the rotational axis. The plunger is movable among at least a locked position and an unlocked position. In the locked position, the plunger urges the swivel gear detent into engagement with the swivel gear and prevents rotation of the swivel gear and attached retractor blade about the rotational axis. In the unlocked position, the plunger permits the swivel gear and attached retractor blade to rotate past the swivel gear detent.

20 Claims, 11 Drawing Sheets

(56) References Cited

U.S. PATENT DOCUMENTS

| | | |
|---|---|---|
| 5,984,865 A | 11/1999 | Farley et al. |
| 5,984,867 A | 11/1999 | Deckman et al. |
| 6,036,641 A | 3/2000 | Taylor |
| 6,074,343 A | 6/2000 | Nathanson et al. |
| 6,315,718 B1 | 11/2001 | Sharratt |
| 6,368,271 B1 | 4/2002 | Sharratt |
| 6,468,207 B1 | 10/2002 | Fowler, Jr. |
| 6,887,198 B2 | 5/2005 | Phillips |
| 6,997,872 B1 | 2/2006 | Bohanan et al. |
| 7,182,731 B2 | 2/2007 | Nguyen |
| 7,892,174 B2 | 2/2011 | Hestad |
| 8,114,020 B2 | 2/2012 | Fricke et al. |
| 8,257,255 B2 | 9/2012 | Farley et al. |
| 8,727,975 B1 | 5/2014 | Pfabe et al. |
| 9,320,506 B2 | 4/2016 | Bertagnoli et al. |
| 9,592,041 B2 | 3/2017 | DeRidder et al. |
| 9,649,101 B2 | 5/2017 | Karpowicz et al. |
| 9,872,675 B2 | 1/2018 | Nowak et al. |
| 2002/0026101 A1 | 2/2002 | Bookwaiter et al. |
| 2002/0095071 A1 | 7/2002 | Farley |
| 2003/0004401 A1 | 1/2003 | Ball et al. |
| 2003/0069478 A1 | 4/2003 | Phillips et al. |
| 2004/0129109 A1 | 7/2004 | Phillips et al. |
| 2004/0199055 A1 | 10/2004 | Mulac et al. |
| 2004/0249388 A1 | 12/2004 | Michelson |
| 2005/0113645 A1 | 5/2005 | Sharratt et al. |
| 2005/0177028 A1 | 8/2005 | Royce et al. |
| 2005/0192484 A1 | 9/2005 | Sharratt et al. |
| 2005/0215866 A1 | 9/2005 | Kim |
| 2006/0178566 A1* | 8/2006 | Fetzer .................. A61B 90/50 600/234 |
| 2006/0224044 A1 | 10/2006 | Marchek et al. |
| 2007/0038033 A1 | 2/2007 | Jones et al. |
| 2007/0270840 A1 | 11/2007 | Chin et al. |
| 2008/0021285 A1 | 1/2008 | Drzyzga et al. |
| 2008/0114209 A1 | 5/2008 | Cohen et al. |
| 2008/0183046 A1 | 7/2008 | Boucher et al. |
| 2008/0188718 A1 | 8/2008 | Spitler et al. |
| 2008/0215081 A1 | 9/2008 | Hsueh et al. |
| 2009/0105547 A1 | 4/2009 | Vayser et al. |
| 2009/0221876 A1 | 9/2009 | Cobb et al. |
| 2010/0217089 A1 | 8/2010 | Farley et al. |
| 2010/0256454 A1 | 10/2010 | Farley et al. |
| 2012/0245431 A1 | 9/2012 | Baudouin et al. |
| 2013/0046147 A1 | 2/2013 | Nichter et al. |
| 2014/0060259 A1 | 3/2014 | Hu |
| 2018/0271509 A1 | 9/2018 | Truckey |

FOREIGN PATENT DOCUMENTS

| | | |
|---|---|---|
| FR | 2690067 | 10/1993 |
| FR | 2807313 | 10/2001 |
| GB | 1570499 | 7/1980 |
| WO | 2019055173 A1 | 3/2019 |

\* cited by examiner

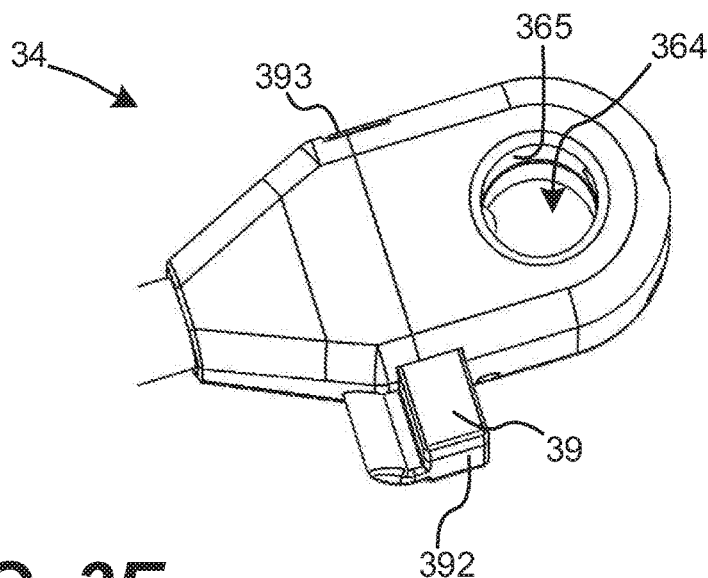
FIG. 3E
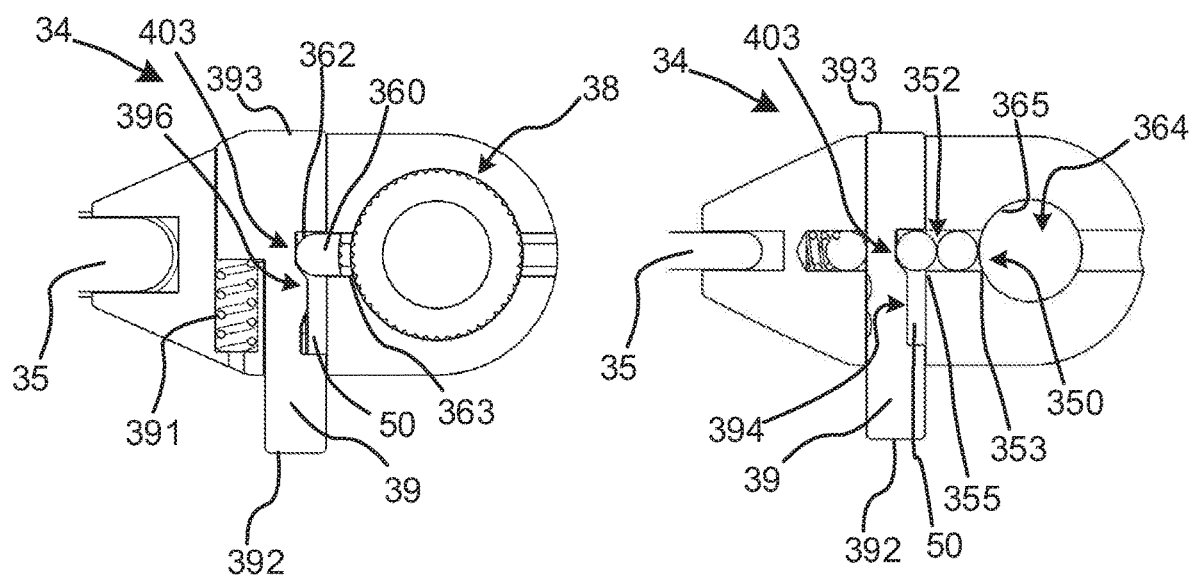
FIG. 3F     FIG. 3G

RETRACTOR SYSTEM, SWIVEL LOCK, AND SURGICAL RETRACTOR BLADE

BACKGROUND

The present disclosure relates to a surgical apparatus that retracts soft tissue and other anatomy of a patient in order to provide access to a surgical site.

During a surgical procedure, a practitioner may make an incision in a patient to access internal organs, bones, and/or other anatomical structures. Surgical retractor blades may be used to hold back soft tissue and other patient anatomy in the immediate area of the incision. Such retractor blades may provide the practitioner with an unobstructed view of the internal organs, bones, and/or other anatomical structures. Furthermore, the retractor blades may provide the practitioner with an opening via which the practitioner may access the anatomical structures with one or more surgical tools.

Further limitations and disadvantages of conventional and traditional approaches will become apparent to one of skill in the art, through comparison of such approaches with the present disclosure.

SUMMARY

Various aspects of the present disclosure provide a retractor system comprising surgical retractor blades that retract anatomy and provide exposure of a surgical site. For example and without limitation, various aspects of the present disclosure are directed to a retractor system having an retractor arm that may be detachably coupled to a surgical retractor blade via a retractor blade connector and its swivel gear. The swivel gear may be locked to prevent rotation or swiveling of the surgical retractor blade with respect to the retractor blade connector. When in an unlocked state or a swivel state, the swivel gear may permit rotation or swiveling of the surgical retractor blade with respect to the retractor blade connector. In some embodiments, the retractor blade connector includes one or more buttons, levers, plungers, and/or other mechanisms which a practitioner may actuate in order to selective switch among a locked state, an unlocked state, and a swivel state without changing the position of the surgical retractor blade with respect to the retractor blade connector.

BRIEF DESCRIPTION OF THE DRAWINGS

FIGS. 3A-3I provide various views of an exemplary retractor blade connector of FIG. 1.

DETAILED DESCRIPTION

Figure 1:
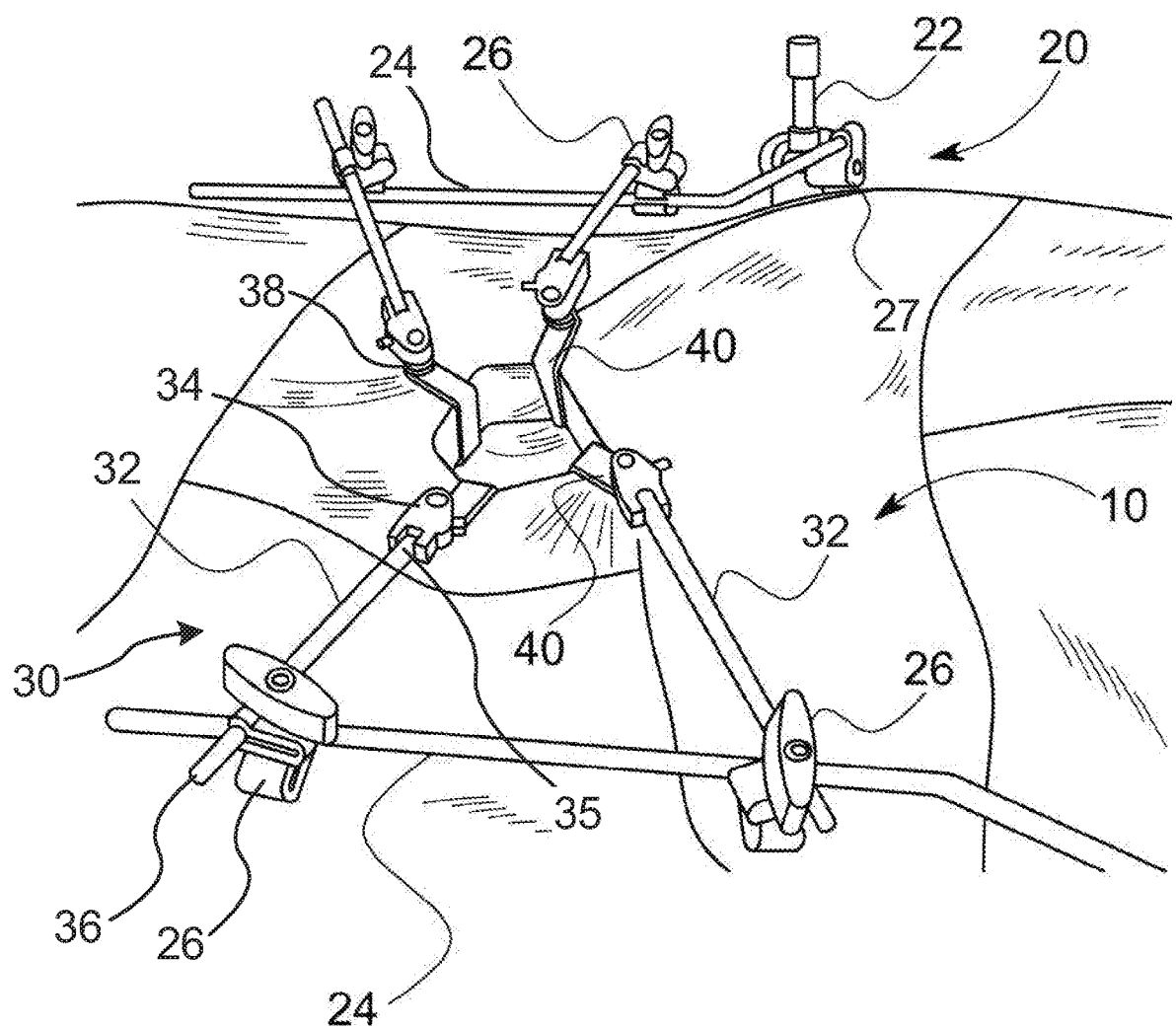
FIG. 1 provides a perspective view of a retractor system in accordance with various aspects of the present disclosure.

Per various aspects of the present disclosure, a retractor system includes a frame to which a proximal end of a retractor arm may be affixed. A distal end of the retractor arm may include a retractor blade connector that detachably couples to an attachment post of a surgical retractor blade and retains the retractor blade in a desired position. In particular, the retractor blade may be inserted into a surgical site and positioned to retract anatomy of the surgical site. A swivel gear of the retractor blade connector may engage the retractor blade and prevent rotation or swiveling of the retractor blade with respect to the retractor blade connector when the swivel gear is in a locked state. The swivel gear may also permit rotation or swiveling of the retractor blade with respect to the retractor blade connector when the swivel gear is in an unlocked state or a swivel state. In some embodiments, the retractor blade connector includes one or more buttons, levers, plungers, and/or other mechanisms which a practitioner may actuate in order to selective switch among locked, unlocked, and swivel states. In certain embodiments, the retractor blade connector may switch among locked, unlocked, and swivel states without disengaging the retractor blade and/or changing the position of a retractor blade with respect to the retractor blade connector.

The following presents details regarding various aspects of the present disclosure by way example. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a semiconductor device may be turned sideways so that its "top" surface is facing horizontally and its "side" surface is facing vertically, without departing from the teachings of the present disclosure.

In the drawings, various dimensions (e.g., lengths, widths, etc.) may be exaggerated for illustrative clarity. Additionally, like reference numbers are utilized to refer to like elements through the discussions of various examples.

Referring now to FIG. 1, an embodiment of a retractor system 10 is illustrated. The retractor system 10 may include a frame assembly 20, one or more retractor arms 30 coupled to the frame assembly 20, and one or more retractor blades 40 coupled to the retractor arms 30. The various components of the retractor system 10 may be made of stainless steel and/or other materials suitable for sterilization.

The frame assembly 20 may include one or more posts 22, frame arms 24, and one or more frame clamps 27. Each post 22 may be fixed to a rail of a hospital bed and/or floor stand such that the post 22 extends upward in a generally vertical direction. Each post 22 may provide a location to which a frame arm 24 may be secured. In the illustrated embodiment, two posts 22 (the second post is out of frame) are secured on opposite sides of a hospital bed, with a frame arm 24 secured to each post 22 by a frame clamp 27. The frame arms 24 may be positioned to generally circumscribe a surgical site. The frame arms 24 may occupy a generally horizontal plane, and may provide a location to which other components of the retractor system 10, such as retractor arms 30 and/or retractor clamps 26, may be affixed.

As further shown, each retractor arm 30 may include an elongated member 32, a retractor blade connector 34, and a retractor clamp 26. The retractor blade connector 34 may be attached to a distal end 35 of the elongated member 32 and a retractor blade 40 may be coupled to the elongated member 32 of the retractor arm 30 via its retractor blade connector 34. A proximal end 36 of the elongated member 32 may pass through a retractor clamp 26. The retractor clamp 26 may clamp or otherwise affix the elongated member 32 to a frame arm 24 of the retractor system 10. In some embodiments, a retractor blade connector 34 may be welded, integrated, or otherwise stationarily affixed to the distal end 35 of the retractor arm 30. In other embodiments, a retractor blade connector 34 may be coupled to the distal end 35 of the retractor arm 30 via a pivot or hinge. In such embodiments, the retractor blade connector 34 may be pivoted or otherwise adjusted with respect to the retractor arm 30 in order to position an attached retractor blade 40 in a desired position.

As explained in greater detail below, each retractor blade connector 34 may include a swivel gear 38 that permits a retractor blade 40 coupled to the retractor blade connector 34 to rotate or swivel about a swivel axis when the swivel gear 38 is in an unlocked state or a swivel state. Conversely, the swivel gear 38 may prevent a retractor blade 40 coupled to the retractor blade connector 34 from rotating or swiveling about the swivel axis when the swivel gear 38 is in a locked state.

As shown, in FIG. 1, the elongated member 32 of the retractor arm 30 includes a single arm portion (e.g., rod, gear rack, tube, etc.) that permits positioning the retractor blade connector 34 and attached retractor blade 40 at a desired distance from a respective frame arm 24. However, the elongated member 32 in some embodiments may comprise a segmented arm having several arm portions (e.g., rods, gear racks, tubes, etc.) that are adjoined to one another via adjustable joints, hinges, and/or angling mechanisms. In such embodiments, the joints, hinges, and/or angling mechanisms may permit adjusting an angle between arm portions of the segmented arm and give the practitioner more freedom in positioning the retractor blade 40 in a desired position.

Figure 2:
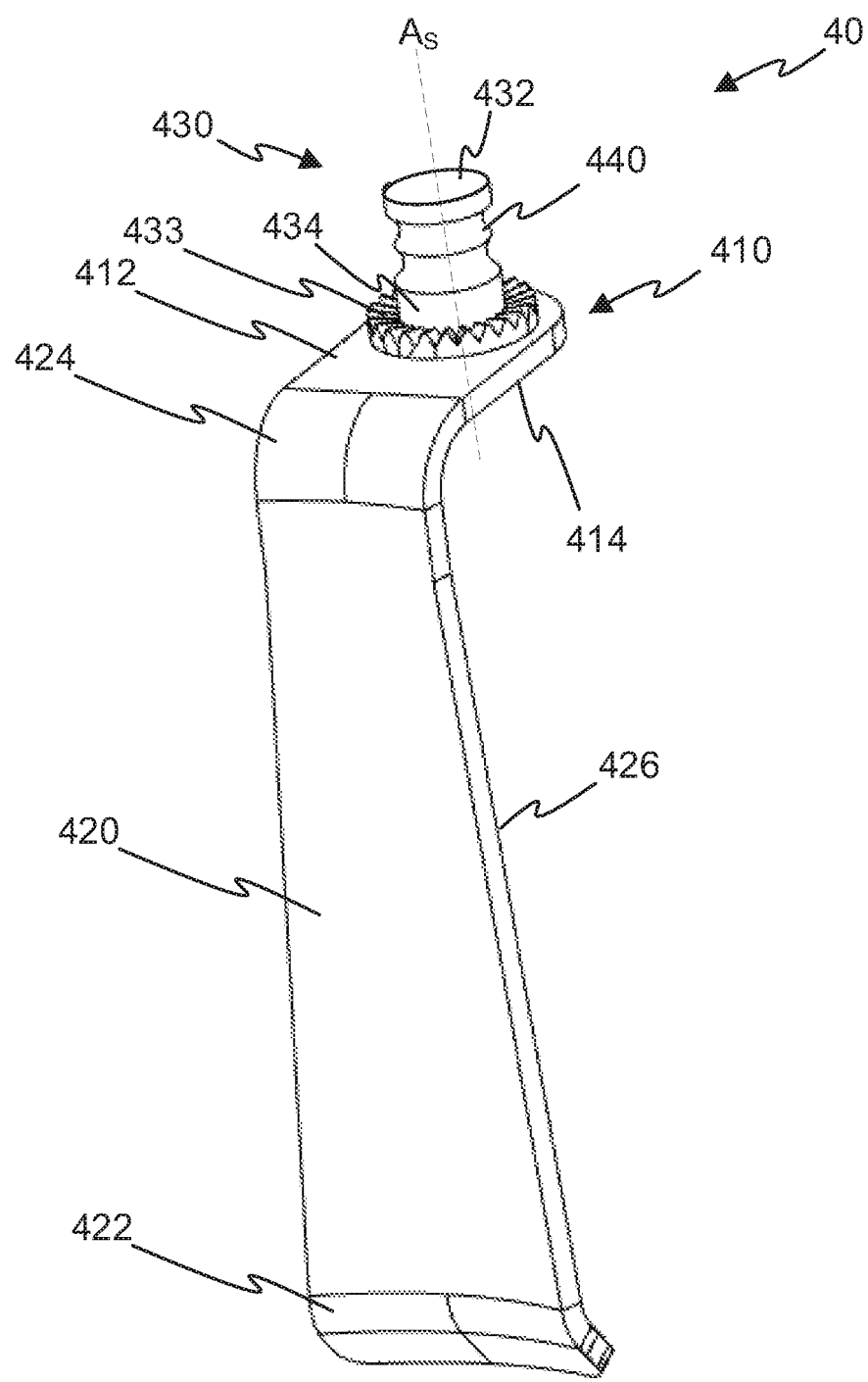
FIG. 2 provides a perspective view of a retractor blade of FIG. 1.

Referring now to FIG. 2, a perspective view of the retractor blade 40 is presented. In general, the retractor blade 40 comprises a retractor body 410 and one or more blades 420 extending from the retractor body 410. Each blade 420 may comprise a smooth, thin plate with dull edges that is inserted into an incision to pull back the tissue. The blades 420 may come in many different sizes depending on the particular application and physical characteristics of the patient. The blades 420 may be slightly curved or completely flat, and may have end prongs of various configurations to make it easier to pull back tissue. In some embodiment, the retractor body 410 and the one or more blades 420 are formed, molded, stamped or otherwise manufactured as a single, integrated unit.

As depicted, the blade 420 may comprise a distal end 422, a proximal end 424, a retracting portion 426. The distal end 422 generally corresponds to the end of the blade 420 inserted into an incision of a patient during a surgical procedure, and the proximal end 424 generally corresponds to the end of the blade 420 extending from the incision and out of the patient during a surgical procedure.

The proximal end 424 of the blade 420 adjoins the retractor body 410, thus resulting in the retracting portion 426 generally extending or projecting from the retractor body 410 toward the distal end 422. As shown, the retracting portion 426 may form a 90° angle with the retractor body 410; however, other angles between the retracting portion 426 and the retractor body 410 are contemplated and may be more suitable for certain surgical procedures. The retracting portion 426 may be sized and adapted to hold back tissue from a surgical site during a procedure. In certain embodiments, the retractor system 10 may include a number of differently sized and/or shaped blades 420 to provide increased adaptability for different procedures and/or patients.

As shown, the retractor body 410 may comprise a generally planar upper surface 412 and a generally planer lower surface 414 that is coplanar with the upper surface 412. The retractor body 410 may further include an attachment post 430. The attachment post 430 may extend upwardly from the upper surface 412 of the retractor body; whereas the blade 420 may extend downwardly from the upper surface 412 of the retractor body 410.

The attachment post 430 may be sized and adapted for attachment to the retractor blade connector 34 of the retractor arm 30. To this end, the attachment post 430 may have a generally cylindrical-shape with a circular cross-section. The attachment post 430 may extend from the upper surface 412 of the retractor body 410. In one embodiment, a longitudinal axis $A_S$ of the attachment post 430 extends at a right angle from the upper surface 412; however, the attachment post 430 in some embodiments may extend from the upper surface 412 at other angles.

The attachment post 430 may include a top surface 432 and a side surface 434. The side surface 434 may include a groove 440. The groove 440 may extend circumferentially around the attachment post 430. The diameter of the attachment post 430 may be sized such that the attachment post 430 may pass through an attachment port 364 of the retractor blade connector 34. See, generally, FIGS. 3A-3I.

The groove 440 may be positioned along the side surface 434 of the attachment post 430 to vertically align the attachment post 430 within the attachment port 364. As explained below, a retractor blade detent 350 or other member of the retractor blade connector 34 may engage the groove 440 to position the attachment post 430 longitudinally within the attachment port 364. The side surface 434 and groove 440 may be tapered and/or rounded. Such tapering and/or rounding may aid or guide the retractor blade detent 350 of the retractor blade connector 34 into engagement with the groove 440, thus helping to longitudinally align the attachment post 430 within the attachment port 364.

As shown in FIG. 2, the retractor blade 40 may include teeth or a serrated surface 433. Similarly, the retractor blade connector 34 may include a swivel gear 38 with teeth or serrated surface 389. See, e.g., FIGS. 3L and 3M. In general, the teeth 389 of the swivel gear 38 and the teeth 433 of the retractor blade 40 are positioned such that the teeth 389, 433 engage each other when the retractor blade 40 is attached to retractor blade connector 34. Such engagement locks the retractor blade 40 to the swivel gear 38 such that the swivel gear 38 and attached retractor blade 40 rotate in unison about the rotational axis $A_S$, if at all. To this end, the teeth 433 of the retractor blade 40 may be positioned along the upper surface 412 of the retractor body 410, along a base of the attachment post 430, or at some other location that permits engagement with teeth 389 of the swivel gear 38 when the retractor blade 40 is attached to retractor blade connector 34. Conversely, teeth 389 of the swivel gear 38 may be positioned on a lower surface of the retractor blade connector 34, along a circumference of the attachment port 364, or at some other location that permits engagement with teeth 433 of the retractor blade 40 when the retractor blade 40 is attached to retractor blade connector 34.

In one embodiment, the groove 440 is positioned along the side surface 434 such that the teeth 389 engage the teeth 433 when the groove 440 is engaged by the retractor blade detent 350 of the retractor blade connector 34. In particular, when the swivel gear 38 is in a locked state, the engaged teeth 389, 433 may prevent rotation or swiveling of the attached retractor blade 40 about a swivel axis $A_S$ of the retractor blade connector 34. Conversely, when the swivel gear 38 is in an unlocked state or a swivel state, the swivel gear 38 may permit rotation or swiveling of the attached retractor blade 40 about the swivel axis $A_S$ despite the teeth 433 of the retractor blade 40 remaining engaged with teeth 389 of the swivel gear 38. Moreover, when the swivel gear 38 is in the unlocked state, the retractor blade 40 may remain attached to the retractor blade connector 34. In particular, the retractor blade detent 350 of the retractor blade connector 34 may continue to engage the groove 440 and prevent the attachment post 430 from being longitudinally withdrawn from the attachment port 364. Thus, by selectively switching between the locked and unlocked state of the swivel gear 38, a practitioner may selectively choose between (i) permitting an attached retractor blade 40 to freely rotate or swivel about the swivel axis $A_S$ and (ii) preventing the attached retractor blade 40 from freely rotating or swiveling about the swivel axis $A_S$.

Figure 3A:
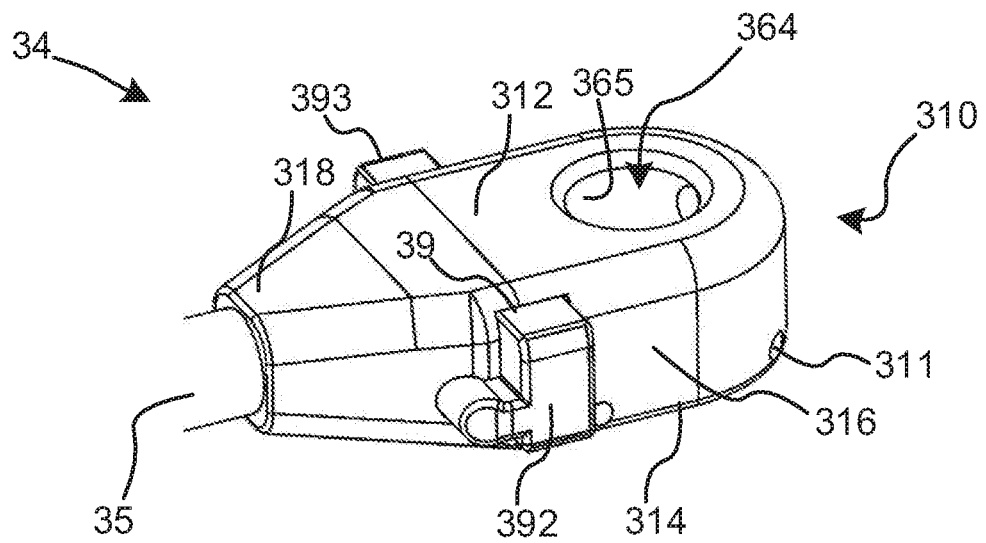
Figure 3B:
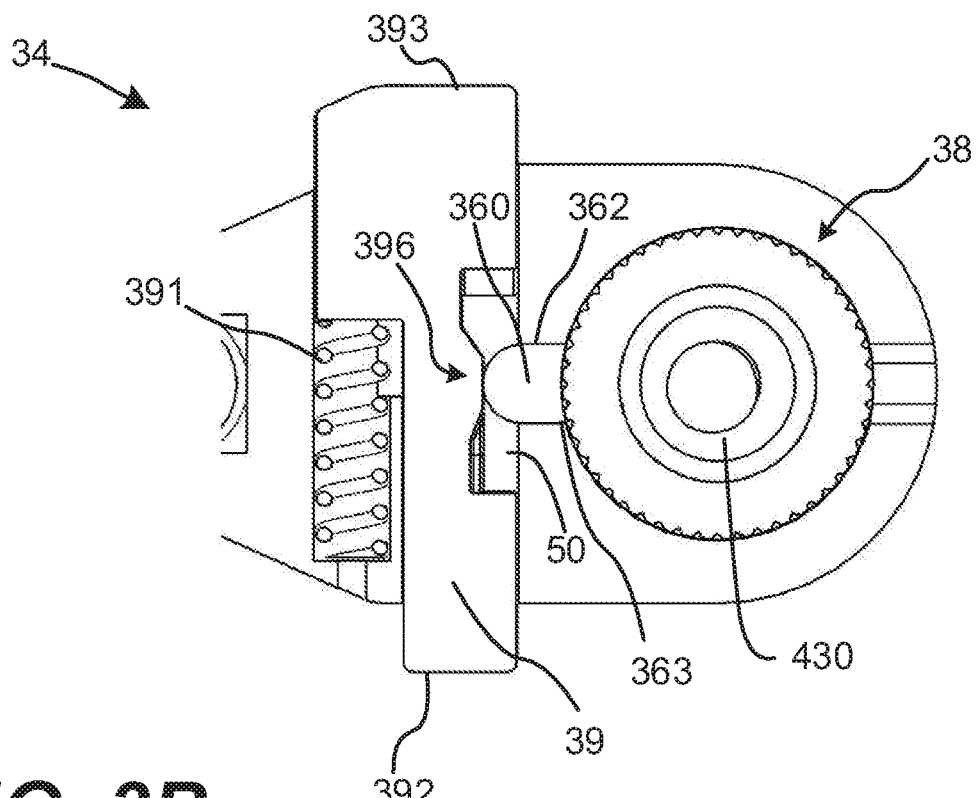
Figure 3C:
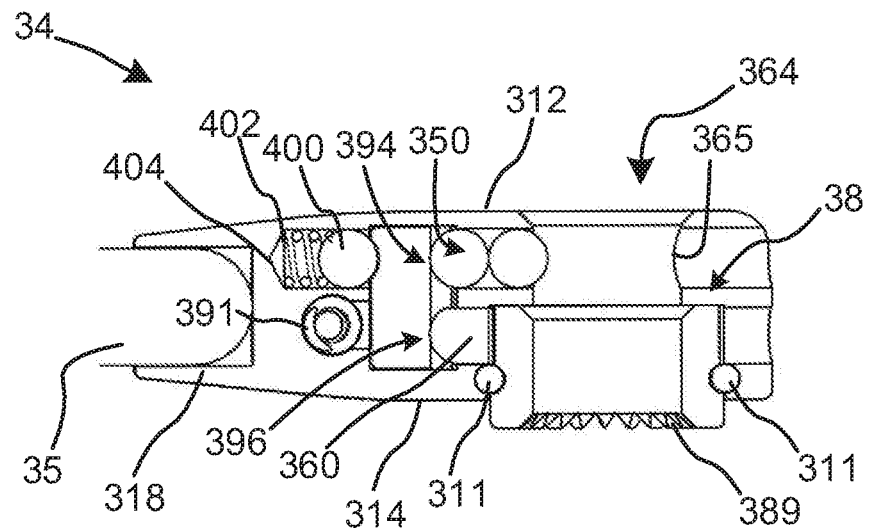
Figure 3D:
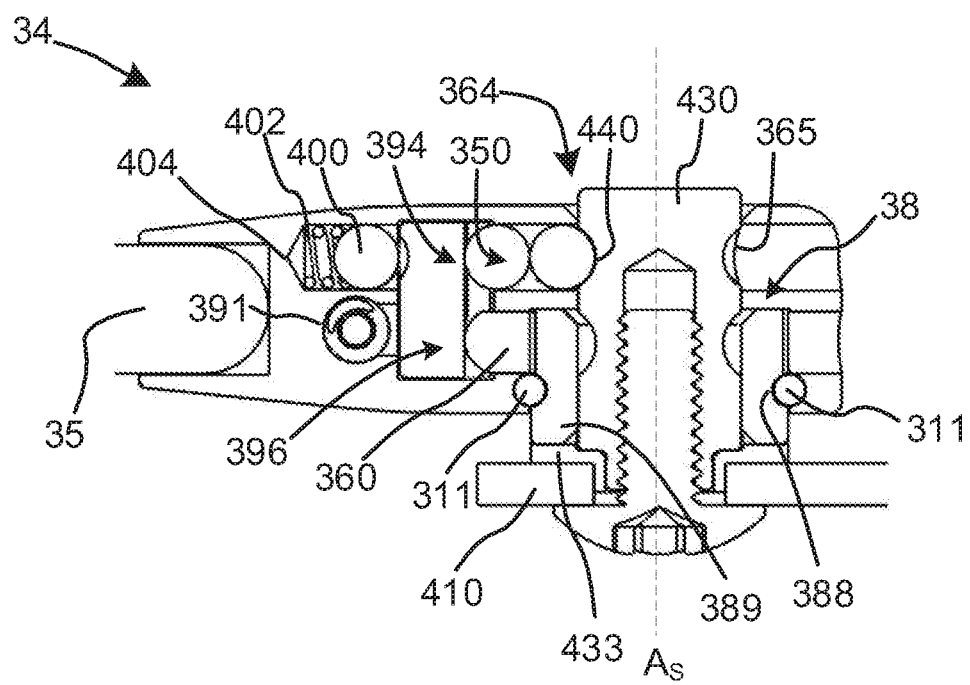
Figure 3H:
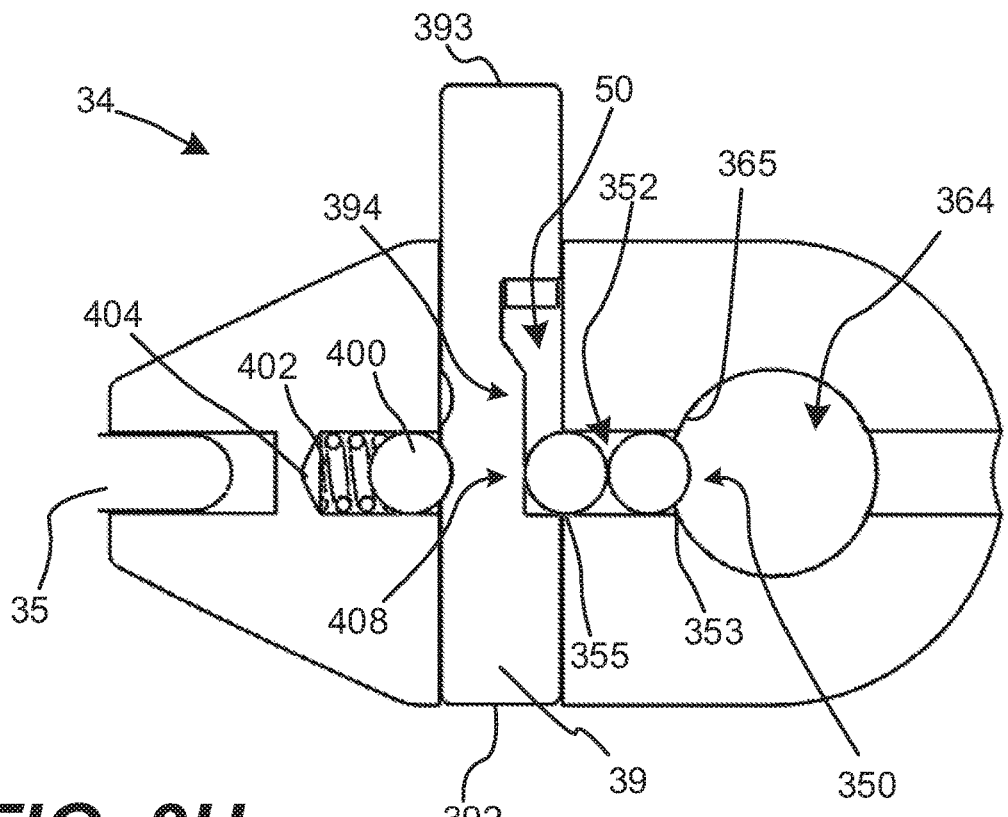
Figure 3I:
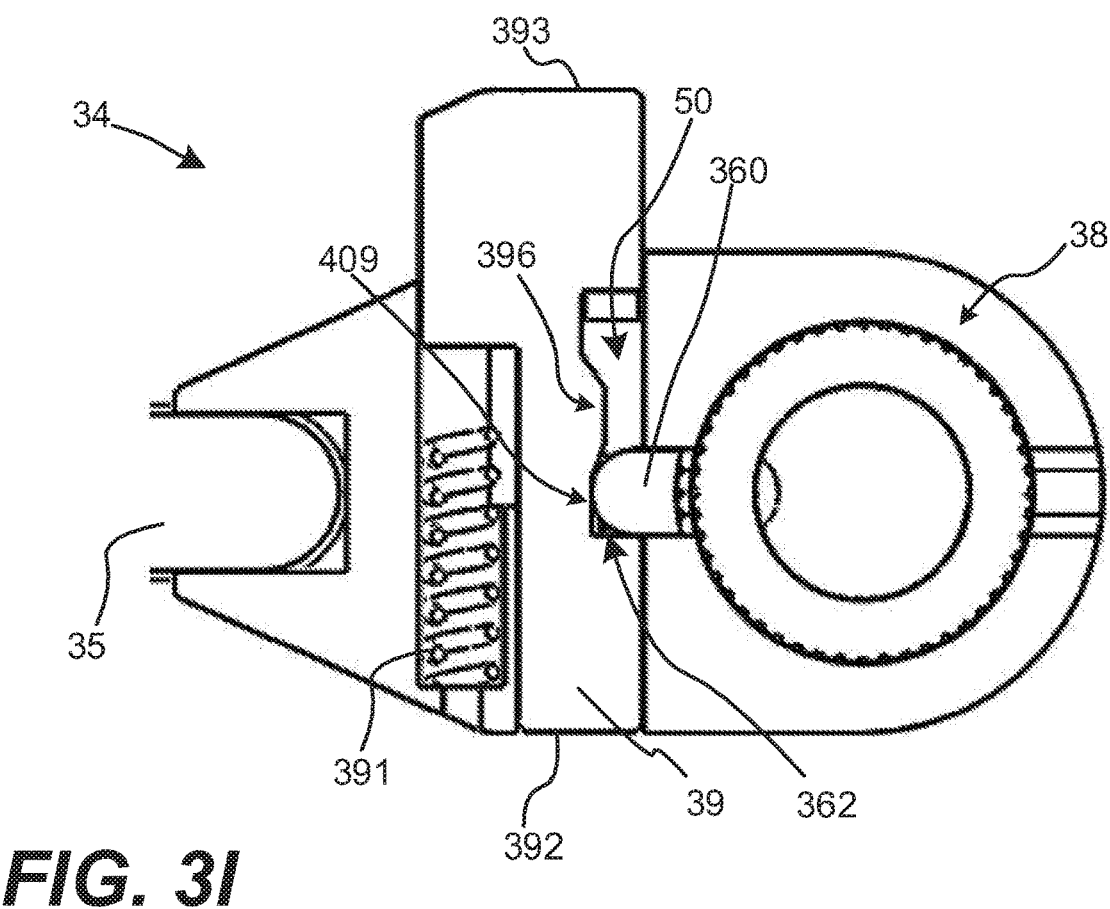
Figure 3J:
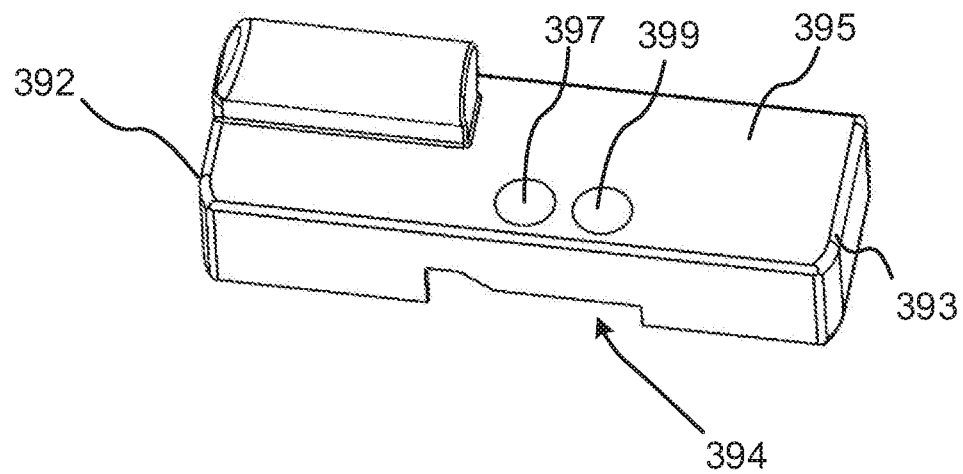
FIGS. 3J-3K provide perspective views of an exemplary plunger of the retractor blade connector of FIGS. 3A-3I.
Figure 3K:
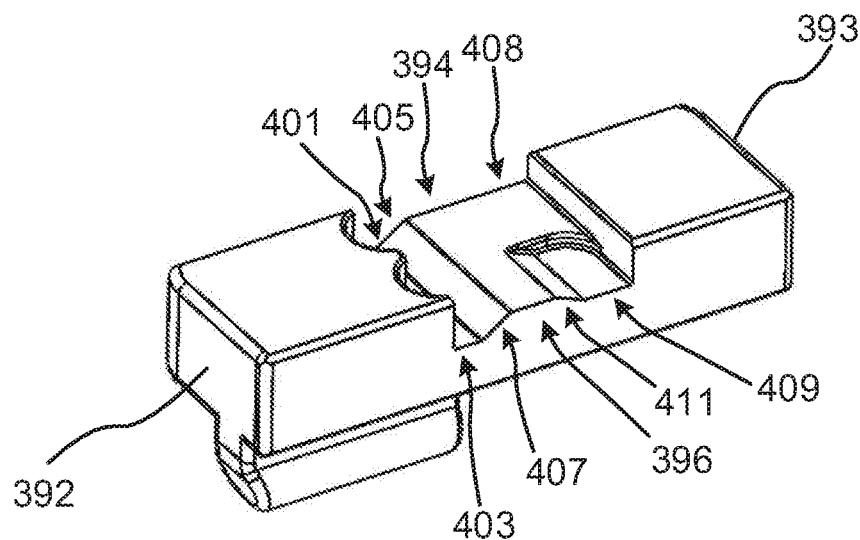
Figure 3L:
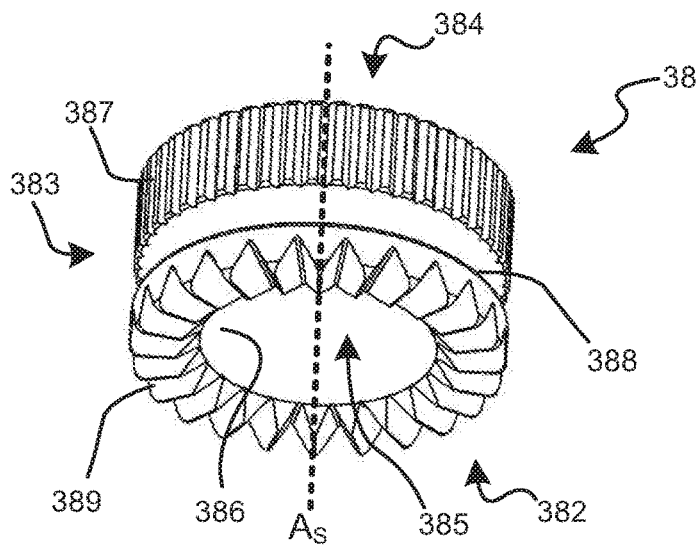
FIGS. 3L-3M provide views of an exemplary swivel gear of the retractor blade connector of FIGS. 3A-3I.
Figure 3N:
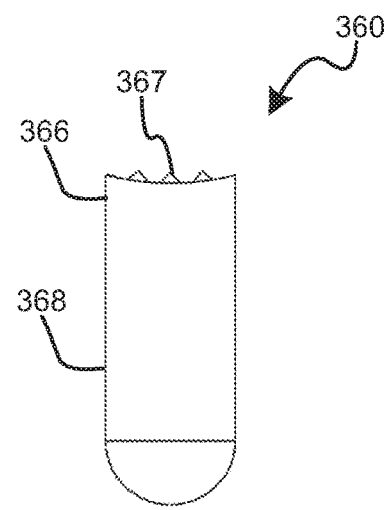
FIGS. 3N-3O provide views of an exemplary swivel gear detent of the retractor blade connector of FIGS. 3A-3I.
Figure 3M:
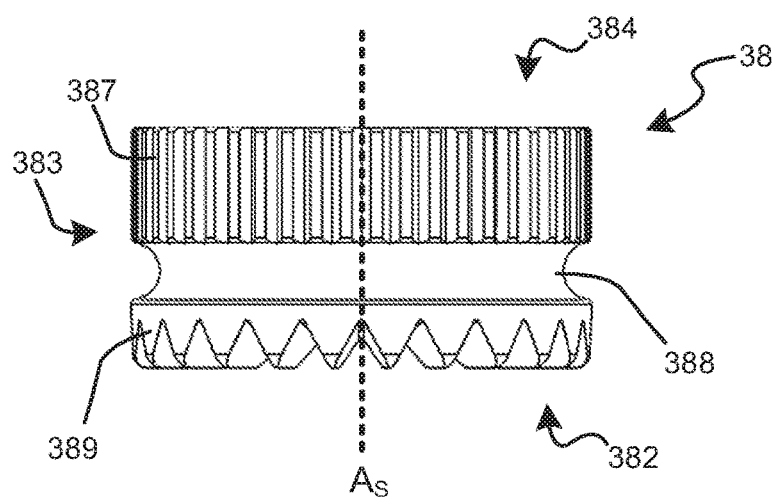
Figure 3O:
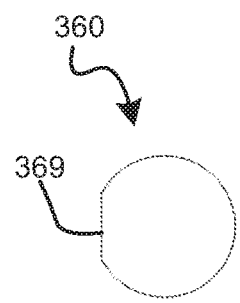

Referring now to FIGS. 3A-3O, one embodiment of a retractor blade connector 34 with a swivel gear 38 is shown. The retractor blade connector 34 may include a housing 310 having an upper surface 312, a lower surface 314, and one or more side surfaces or sidewalls 316 that adjoin the upper surface 312 and the lower surface 314. A proximal end 318 of the housing 310 may be attached to a distal end 35 of a retractor arm 30.

As shown in FIGS. 3C-3D, the retractor blade connector 34 may include an attachment port 364 and an adjoining swivel gear 38. As explained above, the attachment port 364 generally receives the attachment post 430 of a surgical retractor blade 40. As such, the attachment port 364 provides a cylindrical aperture that passes through the upper surface 312 and lower surface 314 of the housing 310. Moreover, the attachment port 364 has a diameter that is slightly larger than the diameter of the attachment post 430. As such, an inner wall 365 of the attachment port 364 may closely mate with the side surface 434 of the attachment post 430 when the attachment post 430 is loaded into the attachment port 364.

Similarly, the swivel gear 38 generally receives the attachment post 430 of a surgical retractor blade 40. As shown in FIGS. 3L and 3M, the swivel gear 38 may include a cylindrical aperture or port 385 that passes through a lower surface 382 and an upper surface 384 of the swivel gear 38. The swivel gear port 385 may have a diameter that is slightly larger than the diameter of the attachment post 430. As such, an inner wall 386 of the swivel gear port 385 may closely mate with the side surface 434 of the attachment post 430 when the attachment post 430 is loaded into the swivel gear port 385.

The swivel gear 38 may further comprise longitudinal sidewalls 383 joining the lower surface 382 to the upper surface 384. The swivel gear port 385 may longitudinally traverse the swivel gear 38 such that the swivel gear port 385 passes through the lower surface 382 and the upper surface 384. The longitudinal sidewalls 383 may include first teeth 387 that extend radially outward from a rotational or swivel axis $A_S$ of the swivel gear 38. The swivel gear 38 may further include second teeth 389 that extend axially downward from the lower surface 382. The swivel gear 38 may also include a groove 388 in the longitudinal sidewall 383. The groove 388 may be positioned in the sidewall 383 between the first teeth 387 and the second teeth 389 and may run circumferentially about the sidewall 383.

As shown in FIGS. 3A-3D, one or more pins 311 may pass through the housing 310. Lateral surfaces of the pins 311 may engage the groove 388 of the swivel gear 38. Via such engagement with the groove 388, the pins 311 may attach the swivel gear 38 to the housing 310 and align the attachment port 364 of the housing 310 with the swivel gear port 385 of the swivel gear 38 such that the ports 364, 385 are coaxial. Moreover, the pins 311 allow the swivel gear 38 to rotate about the swivel axis $A_S$ and restrict coaxial movement of the swivel gear 38 along the attachment port 364.

As further shown in FIGS. 3C and 3D, the retractor blade connector 34 may include a retractor blade detent 350 and a swivel gear detent 360. The retractor blade detent 350 may selectively secure a retractor blade 40 to the retractor blade connector 34 when an attachment post 430 of the retractor blade 40 is loaded through the swivel gear port 385 of the swivel gear 38 and into the attachment port 364 of the retractor blade connector 34. More specifically, the retractor blade detent 350 may selectively engage the attachment post 430 and prevent the attachment post 430 from being longitudinally withdrawn from the attachment port 364 after the attachment post 430 is longitudinally inserted into the attachment port 364. The swivel gear detent 360 may selectively lock the swivel gear 38 and prevent rotation of the swivel gear 38. As explained in greater detail below, such locking of the swivel gear 38 may prevent a retractor blade 40, which is loaded through the swivel gear port 385 of the swivel gear 38 and into the attachment port 364, from rotating about the swivel axis $A_S$ of the swivel gear 38.

The retractor blade detent 350 may be positioned in a retractor blade detent channel 352 that permits the retractor blade detent 350 traverse along the retractor blade detent channel 352. A distal end 353 (See, e.g. FIG. 3G.) of the retractor blade detent channel 352 may provide a retractor blade detent opening in the inner wall 365 of the attachment port 364. The retractor blade detent opening may be longitudinally positioned along the inner wall 365 of the attachment port 364 such that the retractor blade detent opening aligns a distal end of the retractor blade detent 350 with the groove 440 of the attachment post 430 when loaded. Thus, when the retractor blade detent 350 is selectively extended through the retractor blade detent opening, the distal end of the retractor blade detent 350 extends into and engages the groove 440 of the attachment post 430. By engaging the groove 440, the retractor blade detent 350 may prevent the attachment post 430 from being subsequently withdrawn from the attachment port 364. See, e.g., FIG. 3D.

In the depicted embodiment, the retractor blade detent 350 comprises two ball bearings. However, in other embodiments, the retractor blade detent 350 may include other structures such as a different number of ball bearings, a cylindrical rod similar to the swivel gear detent 360, or another structural member that may traverse along the retractor blade detent channel 352 and selectively engage the attachment post 430.

Similarly, the swivel gear detent 360 may be positioned in a swivel gear detent channel 362. The swivel gear detent channel 362 may permit movement of the swivel gear detent 360 along the swivel gear detent channel 362. A distal end 363 of the swivel gear detent channel 362 may provide a swivel gear detent opening that is longitudinally positioned to align a distal end 366 of the swivel gear detent 360 with the radial teeth 387 of the swivel gear 38. Thus, when a distal end 366 of the swivel gear detent 360 is selectively extended through the second opening, one or more teeth 367 at the distal end 366 of the swivel gear detent 360 may engage the radial teeth 387 of the swivel gear 38. See, e.g., FIGS. 3D and 3N. By engaging the teeth 387 of the swivel gear 38, the swivel gear detent 360 may prevent rotation of the swivel gear 38 about its swivel axis $A_S$ and also prevent rotation of a retractor blade 40 engaged with the swivel gear 38.

As shown FIGS. 3N and 3O, the swivel gear detent 360 may have a generally cylindrical shape with a circular cross-section. Moreover, in some embodiments, the swivel gear detent 360 may be keyed to ensure the teeth 367 remain in a desired orientation to ensure proper engagement with teeth 387 of the swivel gear 38. For example, as shown in FIG. 3O, the longitudinal sides 368 may include a flatten or otherwise keyed portion 369 that closely mates with a similarly keyed swivel gear detent channel 362. Such keying ensures the swivel gear detent 360 does not rotate within the swivel gear detent channel 362 and the teeth 367 align with teeth 387 of the swivel gear 38.

In the depicted embodiment, the swivel gear detent 360 comprises a rod-like, cylindrical member, which is shown in greater detail in FIGS. 3N-3O. However, in other embodiments, the retractor blade detent 350 may include other structures such as one or more ball bearings and/or or another structural member that may traverse along the swivel gear detent channel 362 and selectively engage the swivel gear 38. An embodiment in which the swivel gear detent 360 comprises a ball bearing is described below with respect to FIGS. 4A-4D.

As further shown in FIGS. 3A-3G, the retractor blade connector 34 may include a plunger 39 and a plunger channel 50 that passes through sidewalls 316 of housing 310. The plunger channel 50 may permit movement of the plunger 39 along the plunger channel 50. The plunger channel 50 may intersect the retractor blade detent channel 352 and the swivel gear detent channel 362 so that the plunger 39 may interact with the retractor blade detent 350 and the swivel gear detent 360. In one embodiment, the plunger 39 may be slid or urged along the plunger channel 50 via forces applied by plunger biasing spring 391 and/or forces applied to distal ends 392, 393 by, for example, a practitioner pressing on such ends 392, 393. In one embodiment, such applied forces may selectively move the plunger 39 to one of three positions or states.

A locked position of the plunger 39 is shown in FIGS. 3A-3D. In the locked position, the plunger 39 may place the retractor blade detent 350 and the swivel gear detent 360 in a locked state. An unlocked position of the plunger 39 is shown in FIGS. 3E-3G. In the unlocked position, the plunger 39 may place the retractor blade detent 350 and the swivel gear detent 360 in an unlocked state. A swivel position of the plunger 39 is shown in FIGS. 3H-3I. In the swivel position, the plunger 39 may place the retractor blade detent 350 in a locked state and the swivel gear detent 360 in an unlocked state.

More specifically, in the locked position, the plunger 39 may be positioned along the plunger channel 50 such that a first step 394 of the plunger 39 aligns with the retractor blade detent channel 352 and the retractor blade detent 350, and a second step 396 of the plunger 39 aligns with the swivel gear detent channel 362 and the swivel gear detent 360. FIG. 3K shows the first step 394 and the second step 396 aligned with one another. In particular, the first step 394 and the second step 396 in one embodiment are implemented as co-aligned steps due to the retractor blade detent channel 352 and the swivel gear detent channel 362 being vertically aligned with one another per FIGS. 3C and 3D. However, in some embodiments the retractor blade detent channel 352 and the swivel gear detent channel 362 may not be vertically aligned. For example, the retractor blade detent channel 352 and the swivel gear detent channel 362 may each have a different radially offset about the swivel axis $A_S$. In such embodiments, the first step 394 and the second step 396 may be offset from each other so as to respectively align with the retractor blade detent channel 352 and the swivel gear detent channel 362 when the plunger 39 is positioned in the locked position along the plunger channel 50.

As shown in FIG. 3C, the first step 394 of the plunger 39 may force or urge the retractor blade detent 350 into the attachment port 364 of the retractor blade connector 34. As shown in FIG. 3D, forcing the retractor blade detent 350 into the attachment port 364 when attachment post 430 is loaded in the attachment port 364 results in the retractor blade detent 350 entering the groove 440 of the attachment post 430 and engaging the attachment post 430. As is clear from FIG. 3D, the engaged retractor blade detent 350 prevents the attachment post 430 from being longitudinally withdrawn (e.g., in a downward direction of FIG. 3D) from the attachment port 364 since the attachment post 430 is unable to slide past the retractor blade detent 350.

As shown in FIGS. 3B-3D, the second step 396 of the plunger 39 may force or urge the swivel gear detent 360 toward the attachment port 364 and into the swivel gear 38. Forcing the swivel gear detent 360 into swivel gear 38, causes one or more teeth 367 of the swivel gear detent 360 to engage one or more teeth 387 of the swivel gear 374. Such engagement prevents rotation of the swivel gear 38 about is swivel axis $A_S$ since the teeth 387 of the swivel gear 38 are unable to rotate past the teeth 367 of the swivel gear detent 360. As shown in FIG. 3D, the axial teeth 389 of the swivel gear 38 engage teeth 433 of the retractor blade 40 when the retractor blade 40 is attached to retractor blade connector 34. Thus, such engagement of the swivel gear detent 360 with the swivel gear 38 may prevent the attached retractor blade 40 from rotating about the swivel axis $A_S$ due to (i) the swivel gear detent 360 preventing rotation of the swivel gear 38 and its axial teeth 389, and (ii) the teeth of the retractor blade 40 being unable to rotate past the axial teeth 389 which are held in place by the swivel gear detent 360.

As further shown in FIGS. 3C and 3D, the retractor blade connector 34 may include a plunger detent 400 and a plunger detent biasing spring 402 in a plunger detent channel 404. In general, the plunger detent 400 is configured to retain the plunger 39 in one or more positions. To this end, the plunger detent biasing spring 402 may be compressed and positioned between the plunger detent 400 and a proximal end of the plunger detent channel 404. As a result of such compression, the plunger detent biasing spring 402 may urge or force the plunger detent 400 toward a distal end of the plunger detent channel 404 and into a backside surface 395 of the plunger 39.

As shown in FIG. 3J, the backside 395 of the plunger 39 may include a first depression 397 associated with the locked position of the plunger 39 and a second depression 399 associated with the swivel position of the plunger 39. In particular, the first depression 397 is positioned along the backside 395 of the plunger 39 such that the first depression 397 aligns with the plunger detent channel 404 when the plunger 39 is in the locked position. Similarly, the second depression 399 is positioned along the backside 395 of the plunger 39 such that the second depression 399 aligns with the plunger detent channel 404 when the plunger 39 is in the swivel position. As such, the plunger detent biasing spring 402 respectively urges the plunger detent 400 into the first depression 397 and the second depression 399 when the plunger 39 is respectively in the locked position and the swivel position. Accordingly, the plunger detent biasing spring 402 and plunger detent 400 may hold the plunger 39 in these two positions until someone such as the practitioner presses either distal end 392, 393 of the plunger 39 with a force sufficient to overcome the force of the plunger detent biasing spring 402, thus permitting the plunger 39 to be slid past the plunger detent 400 and into a new position.

Of note, the backside 395 of the plunger 39 in the embodiment of FIG. 3J does not include a depression associated with the unlocked position. Instead, the retractor blade connector 34 further includes a plunger biasing spring 391 in the plunger channel 50. See, e.g., FIGS. 3B and 3F. As shown, the plunger biasing spring 391 is positioned between an end of the plunger channel 50 and the plunger 39. Due to such placement of the plunger biasing spring 391, the plunger biasing spring 391 forces or urges the plunger 39 away from the unlocked position shown in FIGS. 3E-3F toward the locked position shown in FIGS. 3A-3D. As such, in order to load the attachment port 364 with an attachment post 430 of a retractor blade 40, someone such as the practitioner may press and hold the plunger 39 in the unlocked position. Once loaded, the practitioner may release the plunger 39 allowing the plunger biasing spring 391 to move or force the plunger 39 to the locked position. In some embodiments, the retractor blade connector 34 may make an audible click as the retractor blade detent 350, swivel gear detent 360, and/or plunger detent 400 respectively engage and snap into place with respective grooves/recesses of the attachment post 430, the swivel gear 38, and the plunger 39. Such an audible clicks may provide cues to the practitioner that the plunger 39 is fully positioned into one of the locked, swivel, and unlocked positions.

Referring now to FIGS. 3E-3G, further details of the unlocked position are presented. More specifically, in the unlocked position, the plunger 39 may be positioned along the plunger channel 50 such that a first recess 401 of the plunger 39 aligns with the retractor blade detent channel 352 and the retractor blade detent 350, and a second recess 403 of the plunger 39 aligns with the swivel gear detent channel 362 and the swivel gear detent 360. By aligning the first recess 401 with the retractor blade detent channel 352, the retractor blade detent 350 move away from the attachment port 364 as shown in FIG. 3G. As such, the retractor blade detent 350 may disengage the groove 440 of an attachment post 430 loaded in the attachment port 364 and permit the attachment post 430 to slide past. Similarly, by aligning the second recess 403 with the swivel gear detent channel 362, the swivel gear detent 360 move away from the attachment port 364 as shown in FIG. 3F. As such, the swivel gear detent 360 may permit teeth 387 of the swivel gear 38 to move past teeth 367 of the swivel gear detent 360 and thus permit the swivel gear 374 to swivel or rotate about the swivel axis $A_S$ as an attachment post 430 is loaded into the attachment port 364.

FIG. 3K shows the first recess 401 and the second recess 403 aligned with one another. In particular, the first recess 401 and the second recess 403 in one embodiment are implemented as co-aligned recesses due to the retractor blade detent channel 352 and the swivel gear detent channel 362 being vertically aligned with one another per FIGS. 3C and 3D. However, in some embodiments the retractor blade detent channel 352 and the swivel gear detent channel 362 may not be vertically aligned. For example, the retractor blade detent channel 352 and the swivel gear detent channel 362 may each have a different radially offset about the swivel axis $A_S$. In such embodiments, the first recess 401 and the second recess 403 may be offset from each other so as to respectively align with the retractor blade detent channel 352 and the swivel gear detent channel 362 when the plunger 39 is positioned in the unlocked position along the plunger channel 50.

FIG. 3K further shows inclines or ramps 405, 407 that respectively couple the first recess 401 with the first step 394 and the second recess 403 with the second step 396. In particular, the first ramp 405 provides a gradual transition or incline between the first recess 401 and the first step 394. Such gradual incline enables the plunger 39 to urge the retractor blade detent 350 from the first recess 401 to the first step 394 as the plunger 39 traverses the plunger channel 50. Similarly, the second ramp 407 provides a gradual transition or incline between the second recess 403 and the second step 396. Such gradual incline enables the plunger 39 to urge the swivel gear detent 360 from the second recess 403 to the second step 396 as the plunger 39 traverses the plunger channel 50.

As noted above, the backside 395 of the plunger 39 in the embodiment of FIG. 3J does not include a depression associated with the unlocked position. As such, the plunger detent 400 may engage the backside 395 of the plunger 39, but not either depression 397, 399 when in the unlocked position. See, e.g., FIG. 3G. When the practitioner stops pressing the distal end 393 of the plunger 39, the plunger biasing spring 391 may cause the plunger 39 to move away from the unlocked position of FIGS. 3E-3G and into the locked position of FIGS. 3A-3D. Upon achieving the locked position, the plunger detent biasing spring 402 may cause the plunger detent 400 to engage the depression 397 in the backside 395 and may stop the plunger biasing spring 391 from further moving the plunger 39 away from the unlocked position.

Referring now to FIGS. 3H and 3I, further details of the swivel position are presented. More specifically, in the swivel position, the plunger 39 may be positioned along the plunger channel 50 such that a third step 408 of the plunger 39 aligns with the retractor blade detent channel 352 and the retractor blade detent 350, and a third recess 409 of the plunger 39 aligns with the swivel gear detent channel 362 and the swivel gear detent 360. By aligning the third step 408 with the retractor blade detent channel 352, the retractor blade detent 350 remains extended into the attachment port 364. See, e.g., FIGS. 3C and 3H. As such, the retractor blade detent 350 may engage the groove 440 of an attachment post 430 loaded in the attachment port 364 and prevent the attachment post 430 from being withdrawn from the attachment port 364. Conversely, by aligning the third recess 409 with the swivel gear detent channel 362, the swivel gear detent 360 may be moved away from the attachment port 364 as shown in FIG. 3I. As such, the swivel gear detent 360 may permit teeth 387 of the swivel gear 38 to move past teeth 367 of the swivel gear detent 360 and thus permit the swivel gear 38 and a retractor blade 40 engaged with the swivel gear 38 to swivel or rotate about the swivel axis $A_S$.

FIG. 3K further shows a third ramp 411 that couples the third recess 409 with the second step 396. In particular, the third ramp 411 provides a gradual transition or incline between the third recess 409 and the second step 396. Such gradual incline enables the plunger 39 to urge the swivel gear detent 360 from the third recess 409 to the second step 398 as the plunger 39 traverses the plunger channel 50.

As noted above, the backside 395 of the plunger 39 may include a second depression 399 associated with the swivel position of the plunger 39. In particular, the second depression 399 is positioned along the backside 395 of the plunger 39 such that the second depression 399 aligns with the plunger detent channel 404 when the plunger 39 is in the swivel position. As such, the plunger detent biasing spring 402 respectively urges the plunger detent 400 into the second depression 399 when the plunger 39 is in the swivel position. See, e.g., FIG. 3H. Accordingly, the plunger detent biasing spring 402 and plunger detent 400 may hold the plunger 39 in the swivel position until someone such as the practitioner presses distal end 392 of the plunger 39 with a force sufficient to overcome the force of the plunger detent biasing spring 402, thus permitting the plunger 39 to be slid past the plunger detent 400 and into the locked position.

Figure 4A:
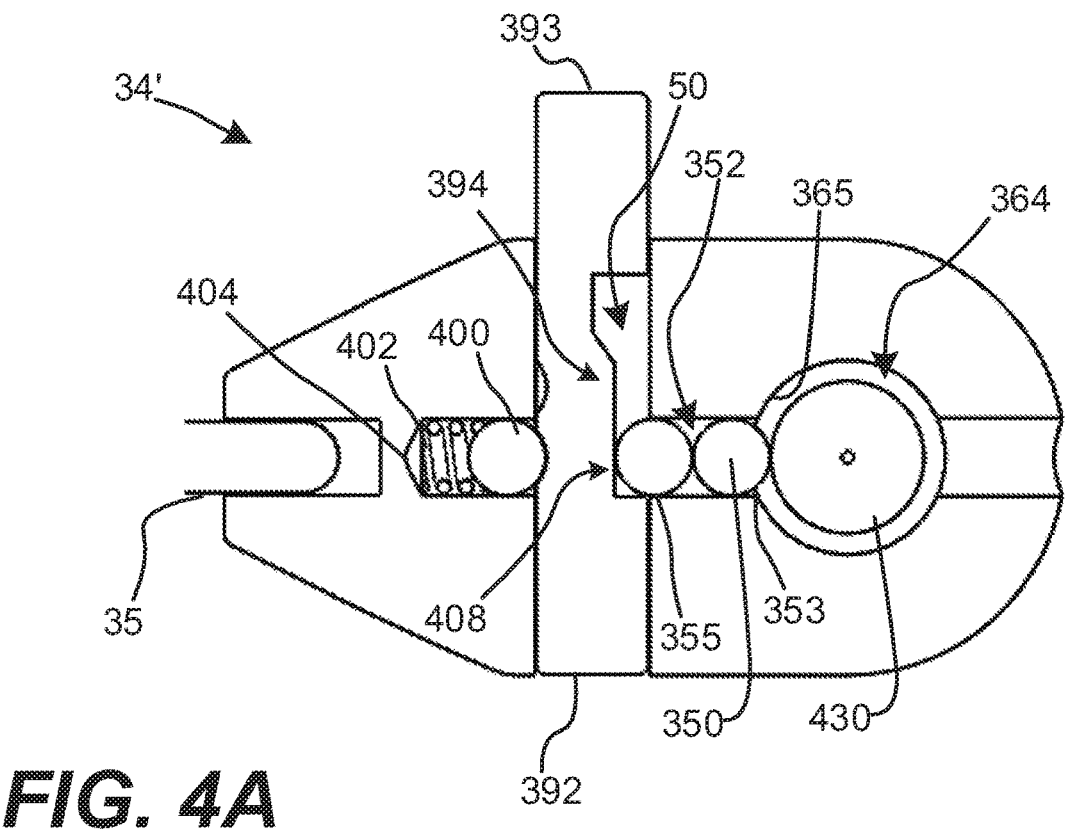
FIGS. 4A-4B provide various views of another exemplary retractor blade connector of FIG. 1.
Figure 4B:
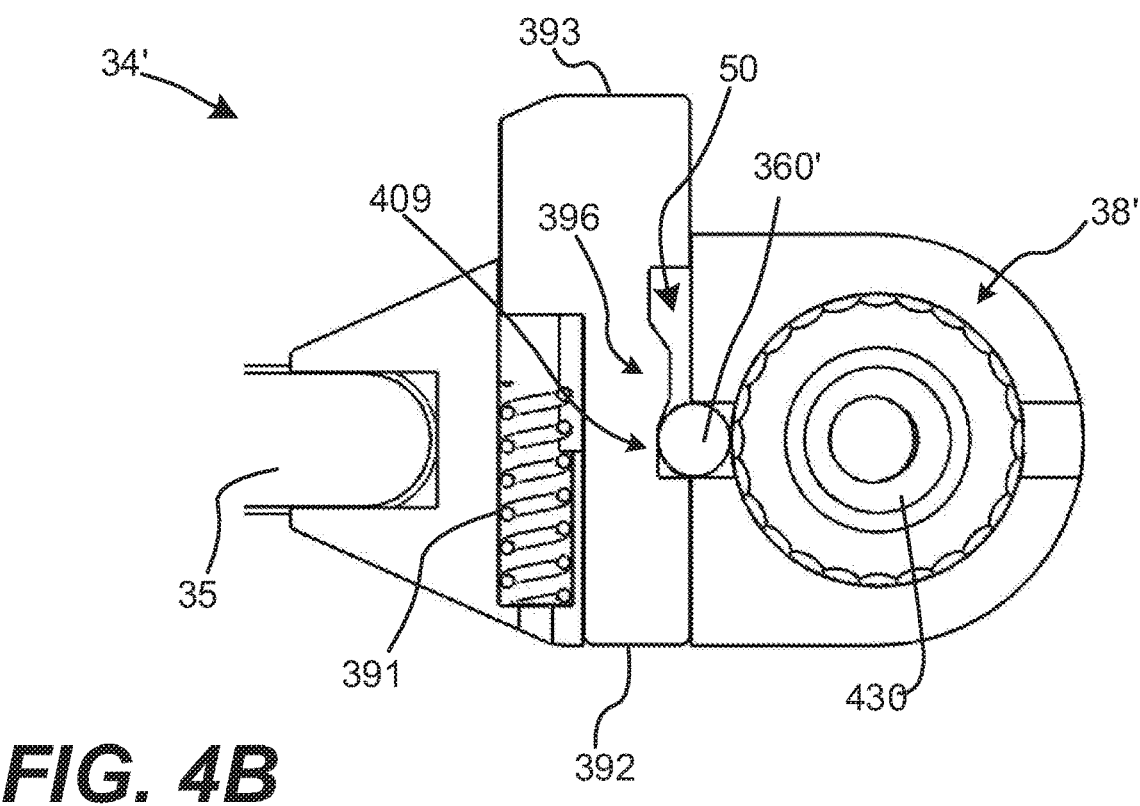
Figure 4C:
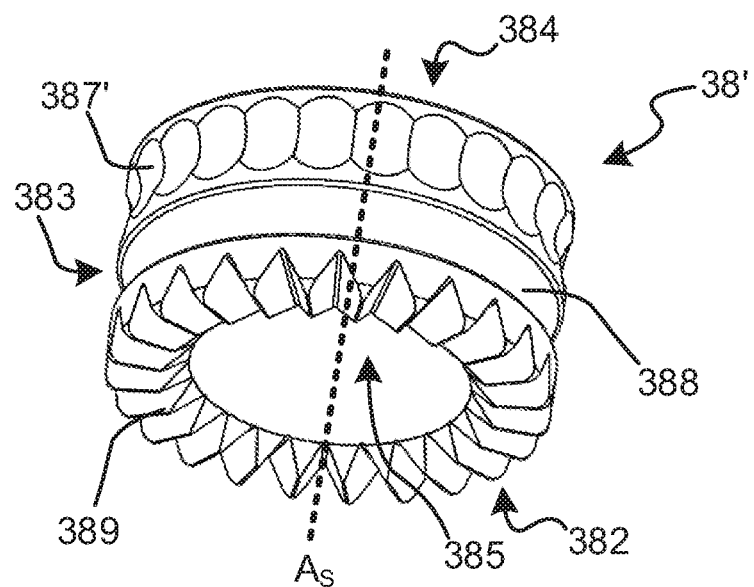
FIGS. 4C-4D provide views of an exemplary swivel gear of the retractor blade connector of FIGS. 4A-4B.
Figure 4D:
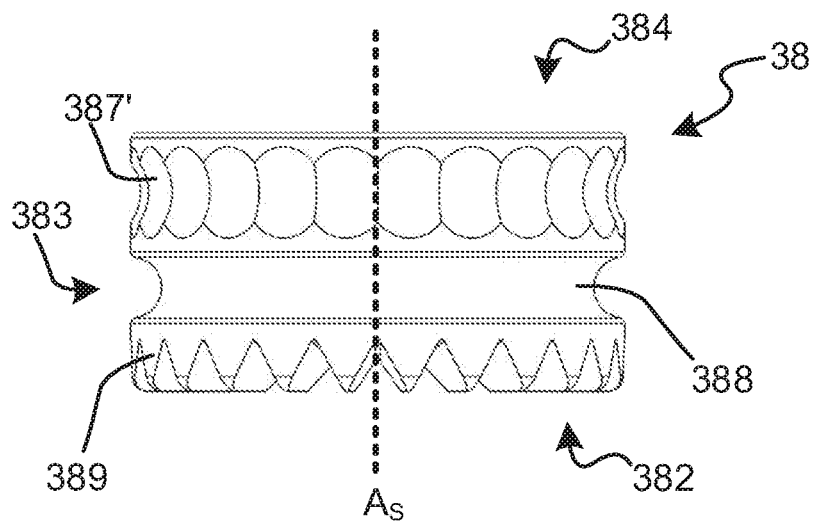

Referring now to FIGS. 4A-4D, another embodiment of a retractor blade connector 34' is shown. In general, the retractor blade connector 34' operates in a manner similar to the retractor blade connector 34. As such, similar aspects of the retractor blade connector 34' are labeled with reference numerals similar to those used to label retractor blade connector 34. However, the retractor blade connector 34' utilizes a swivel gear detent 360' of one or more ball bearings instead of the swivel gear detent 360 of FIGS. 3N-3O. As such, the swivel gear 38' of the retractor blade connector 34' includes a circumferential ring of spherical depressions 387' as shown in FIGS. 4C-4D, which effectively replace the radially teeth 387 of the swivel gear 38 shown in FIGS. 3L-3M. The spherical depressions 387' are sized to engage and closely mate with a ball bearing of the swivel gear detent 360' when the plunger 39 is in the locked position. Due to such engagement, the swivel gear detent 360' may lock or prevent the swivel gear 38' from rotating about its swivel axis $A_S$ when the plunger 39 is in the locked position. Moreover, the swivel gear detent 306' may disengage from the depressions 387' and permit the swivel gear 38' to rotate about its swivel axis $A_S$ when the plunger 39 is in the swivel position or the unlocked position.

Figure 5A:
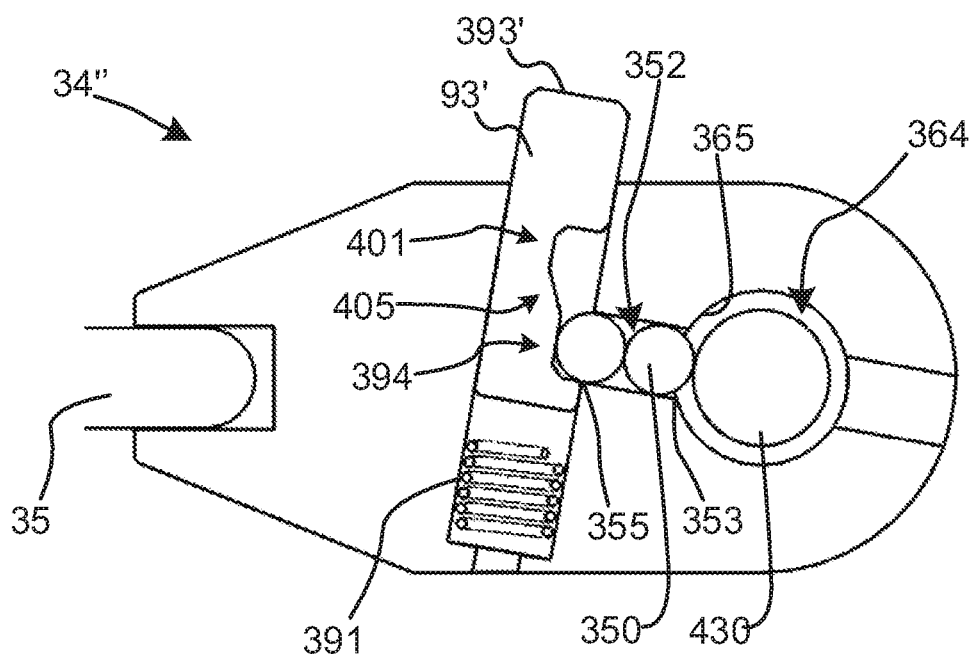
FIGS. 5A-5B provide various views of yet another exemplary retractor blade connector of FIG. 1.
Figure 5B:
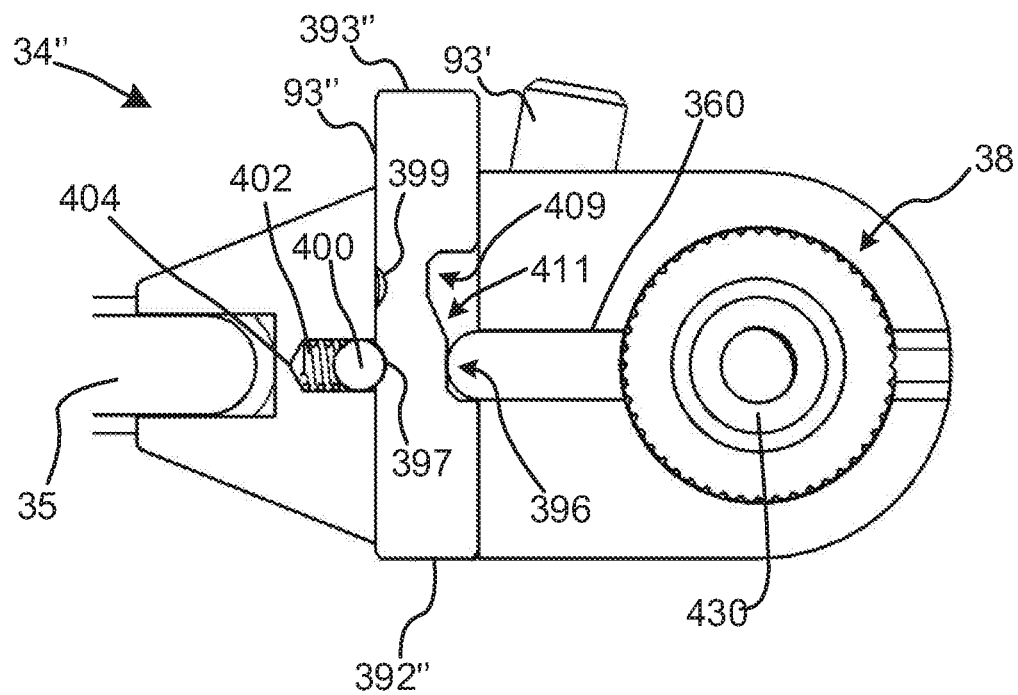

Referring now to FIGS. 5A-5B, yet another embodiment of a retractor blade connector 34" is shown. In general, the retractor blade connector 34" operates in a manner similar to the retractor blade connector 34. As such, similar aspects of the retractor blade connector 34" are labeled with reference numerals similar to those used to label retractor blade connector 34. However, the retractor blade connector 34" utilizes a first plunger 39' and a second plunger 39" instead of the single plunger 39 of FIGS. 3J-3K. In particular, the first plunger 39' operates the retractor blade detent 350 in a manner similar to the operation of the plunger 39 of FIGS. 3J-3K. To this end, the first plunger 39' essentially includes the first step 394, the first recess 401, and the first ramp 405 of the plunger 39. The plunger biasing spring 391 biases the first plunger 39' toward a locked position in which the first step 394 is aligned with the retractor blade detent 350 and urges the first detent into engagement with the attachment post 430. To disengage the retractor blade detent 350, a practitioner may press and hold distal end 393' of the first plunger 39' so as to align the first recess 401 with the retractor blade detent 350. While holding the first plunger 39' in the unlocked position, the practitioner may load and/or unload an attachment post 430 of a retractor blade 40 from the attachment port 364. Upon release of distal end 393' of the first plunger 39', the plunger biasing spring 391 may return the first plunger 39' to the locked position.

The second plunger 39" operates the swivel gear detent 360 in a manner similar to the operation of the plunger 39 of FIGS. 3A-3K. To this end, the second plunger 39" essentially includes the second step 396, the first depression 397, the second depression 399, the third recess 409, and the third ramp 411 of the plunger 39. In general, the second plunger 39" may be placed in a locked position in which the plunger detent 400 engages the first depression 397 or in an unlocked position in which the plunger detent 400 engages the second depression 399. The plunger detent 400 and the plunger detent biasing spring 402 may retain the second plunger 39" in its respective position until a force applied to a distal end 392", 393" of the second plunger 39" is sufficient to overcome the plunger detent 400.

FIG. 5B depicts the second plunger 39" in a locked position. As such, the second step 396 is aligned with the swivel gear detent 360 thus causing the swivel gear detent 360 to engage the swivel gear 38. In such position, the swivel gear detent 360 prevents the swivel gear 38 and any retractor blade 40 engaged with the swivel gear 38 from rotating about the swivel axis $A_S$. A practitioner may press the distal end 393" of the second plunger 39" to cause the second plunger 39" to traverse a second plunger channel 50' until the third recess 409 aligns with the swivel gear detent 360. In such position, the swivel gear detent 360 may be urged away from the swivel gear 38 so as to permit the swivel gear 38 and any retractor blade 40 engaged with the swivel gear 38 to rotate about the swivel axis $A_S$. Conversely, when in a swivel position, a practitioner may press the distal end 392" of the second plunger 39" to cause the second plunger 39" to traverse a second plunger channel 50' until the second step 396 aligns with the swivel gear detent 360. In such position, the swivel gear detent 360 may be urged into engagement with the swivel gear 38 and prevent the swivel gear 38 and any retractor blade 40 engaged with the swivel gear 38 from rotating about the swivel axis $A_S$.

While particular embodiments of the present disclosure have been shown, it will be understood that the appended claims are not limited thereto since modifications may be made by those skilled in the art, particularly in light of the foregoing teaching. It is therefore, the appended claims that define the true spirit and scope of the present disclosure and its embodiments.

What is claimed is:

1. A retractor blade connector, comprising:
a swivel gear comprising a swivel gear port and a rotational axis, wherein the swivel gear engages a retractor blade when an attachment post of the retractor blade is inserted into the swivel gear port;
a swivel gear detent positioned to selectively engage the swivel gear and prevent the swivel gear and attached retractor blade from rotating about the rotational axis;
a retractor blade detent positioned to selectively engage the attachment post of the retractor blade when the attachment post is inserted through the swivel gear port,
a first plunger movable among at least:
   a locked position in which the first plunger urges the swivel gear detent into engagement with the swivel gear and prevents rotation of the swivel gear and attached retractor blade about the rotational axis, wherein the locked position of the first plunger causes the first plunger to urge the retractor blade detent into engagement with the attachment post of the retractor blade and prevents withdrawal of the attachment post of the retractor blade when the attachment post is inserted through the swivel gear port; and
   an unlocked position in which the first plunger permits the swivel gear and attached retractor blade to rotate past the swivel gear detent; and
   a swivel position in which the first plunger permits the swivel gear to rotate past the swivel gear detent and the first plunger urges the retractor blade detent into engagement with the attachment post of the retractor blade and prevents withdrawal of the attachment post of the retractor blade when the attachment post is inserted through the swivel gear port; and
a biasing spring that biases the first plunger toward the locked position of the first plunger.

2. The retractor blade connector of claim 1, wherein the swivel gear comprises teeth that engage teeth of the retractor blade when the attachment post is inserted into the swivel gear port.

3. The retractor blade connector of claim 1, wherein:
the swivel gear comprises teeth; and
the swivel gear detent engages one or more teeth of the swivel gear when the first plunger is in the locked position.

4. The retractor blade connector of claim 1, wherein:
the swivel gear comprises a circumferential ring of depressions; and
the swivel gear detent engages one or more depressions of the swivel gear when the first plunger is in the locked position.

5. A retractor blade connector, comprising:
a swivel gear comprising a swivel gear port and a rotational axis, wherein the swivel gear engages a retractor blade when an attachment post of the retractor blade is inserted into the swivel gear port;
a swivel gear detent positioned to selectively engage the swivel gear and prevent the swivel gear and attached retractor blade from rotating about the rotational axis; and
a first plunger movable among at least:
   a locked position in which the first plunger urges the swivel gear detent into engagement with the swivel gear and prevents rotation of the swivel gear and attached retractor blade about the rotational axis;
   an unlocked position in which the first plunger permits the swivel gear and attached retractor blade to rotate past the swivel gear detent;
a retractor blade detent positioned to selectively engage the attachment post of the retractor blade when the attachment post is inserted through the swivel gear port; and
a second plunger movable between at least a locked position in which the second plunger urges the retractor blade detent into engagement with the attachment post of the retractor blade and prevents withdrawal of the attachment post of the retractor blade when the attachment post is inserted through the swivel gear port.

6. The retractor blade connector of claim 5, further comprising a biasing spring that biases the second plunger toward the locked position of the second plunger.

7. The retractor blade connector of claim 5, wherein the swivel gear comprises teeth that engage teeth of the retractor blade when the attachment post is inserted into the swivel gear port.

8. The retractor blade connector of claim 5, wherein:
the swivel gear comprises teeth; and
the swivel gear detent engages one or more teeth of the swivel gear when the first plunger is in the locked position.

9. The retractor blade connector of claim 5, wherein:
the swivel gear comprises a circumferential ring of depressions; and
the swivel gear detent engages one or more depressions of the swivel gear when the first plunger is in the locked position.

10. A retractor system, comprising:
a retractor arm comprising an elongated member and a retractor blade connector coupled to an end of the elongated member, the retractor blade connector including a swivel gear comprising a swivel gear port and a rotational axis; and
a retractor blade attached to the retractor arm via the swivel gear, the retractor blade comprising a retractor body, an attachment post extending from the retractor body and through the swivel gear port, and a blade extending from the retractor body;
wherein the retractor blade connector comprises:
   a swivel gear detent positioned to selectively engage the swivel gear and prevent the swivel gear and attached retractor blade from rotating about the rotational axis; and
   a first plunger movable among at least a locked position in which the first plunger urges the swivel gear detent into engagement with the swivel gear and prevents rotation of the swivel gear and attached retractor blade about the rotational axis, and an unlocked position in which the first plunger permits the swivel gear and attached retractor blade to rotate past the swivel gear detent;
   a retractor blade detent positioned to selectively engage a groove in the attachment post of the retractor blade; and
   a second plunger movable between at least a locked position in which the second plunger urges the retractor blade detent into the groove in the attachment post of the retractor blade and prevents withdrawal of the attachment post of the retractor blade.

11. The retractor system of claim 10, wherein the retractor blade connector further comprises a biasing spring that biases the second plunger toward the locked position of the second plunger.

12. The retractor system of claim 11, wherein the retractor blade connector further comprises a biasing spring that biases the first plunger toward the locked position of the first plunger.

13. A retractor system, comprising:
   a retractor arm comprising an elongated member and a retractor blade connector coupled to an end of the elongated member, the retractor blade connector including a swivel gear comprising a swivel gear port and a rotational axis; and
   a retractor blade attached to the retractor arm via the swivel gear, the retractor blade comprising a retractor body, an attachment post extending from the retractor body and through the swivel gear port, and a blade extending from the retractor body;
   wherein the retractor blade connector comprises:
      a swivel gear detent positioned to selectively engage the swivel gear and prevent the swivel gear and attached retractor blade from rotating about the rotational axis; and
      a first plunger movable among at least a locked position in which the first plunger urges the swivel gear detent into engagement with the swivel gear and prevents rotation of the swivel gear and attached retractor blade about the rotational axis, and an unlocked position in which the first plunger permits the swivel gear and attached retractor blade to rotate past the swivel gear detent; and
   wherein the swivel gear comprises axial teeth that engage teeth of the retractor blade and cause the swivel gear and retractor blade to rotate about the rotation axis in unison.

14. The retractor system of claim 13, wherein:
   the swivel gear comprises teeth that extend radially from the rotation axis; and
   the swivel gear detent comprises teeth that engage one or more of the teeth of the swivel gear when the first plunger is in the locked position.

15. The retractor system of claim 13, wherein the retractor blade connector further comprises a retractor blade detent positioned to selectively engage a groove in the attachment post of the retractor blade and prevent withdrawal of the attachment post of the retractor blade.

16. The retractor system of claim 13, wherein:
   the retractor blade connector further comprises a retractor blade detent positioned to selectively engage a groove in the attachment post of the retractor blade; and
   the locked position of the first plunger causes the first plunger to urge the retractor blade detent into the groove of the attachment post of the retractor blade and prevent withdrawal of the attachment post of the retractor blade.

17. The retractor system of claim 13, wherein the retractor blade connector further comprises a biasing spring that biases the first plunger toward the locked position of the first plunger.

18. A retractor system, comprising:
   a retractor arm comprising an elongated member and a retractor blade connector coupled to an end of the elongated member, the retractor blade connector including a swivel gear comprising a swivel gear port and a rotational axis; and
   a retractor blade attached to the retractor arm via the swivel gear, the retractor blade comprising a retractor body, an attachment post extending from the retractor body and through the swivel gear port, and a blade extending from the retractor body;
   wherein the retractor blade connector comprises:
      a swivel gear detent positioned to selectively engage the swivel gear and prevent the swivel gear and attached retractor blade from rotating about the rotational axis; and
      a first plunger movable among at least a locked position in which the first plunger urges the swivel gear detent into engagement with the swivel gear and prevents rotation of the swivel gear and attached retractor blade about the rotational axis, and an unlocked position in which the first plunger permits the swivel gear and attached retractor blade to rotate past the swivel gear detent; and
   wherein the swivel gear comprises a circumferential ring of depressions; and
   wherein the swivel gear detent comprises a ball bearing that engages a depression of the swivel gear when the first plunger is in the locked position.

19. The retractor system of claim 18, wherein the retractor blade connector further comprises a retractor blade detent positioned to selectively engage a groove in the attachment post of the retractor blade and prevent withdrawal of the attachment post of the retractor blade.

20. The retractor system of claim 19, wherein the first plunger is further movable to a swivel position in which:
   the first plunger permits radial teeth of the swivel gear to rotate past teeth of the swivel gear detent; and
   the first plunger urges the retractor blade detent into the groove of the attachment post of the retractor blade and prevents withdrawal of the attachment post of the retractor blade.

\* \* \* \* \*